(12) United States Patent
Uchiyama et al.

(10) Patent No.: US 6,485,415 B1
(45) Date of Patent: Nov. 26, 2002

(54) MEDICAL MONITORING SYSTEM

(75) Inventors: Kazuyuki Uchiyama, Tokyo (JP);
Masatoshi Yanagidaira, Tokyo (JP);
Mitsuo Yasushi, Tokyo (JP); Hiroshi Satoh, Tokyo (JP)

(73) Assignee: Pioneer Corporation, Tokyo (JP)

( * ) Notice: Subject to any disclaimer, the term of this patent is extended or adjusted under 35 U.S.C. 154(b) by 0 days.

(21) Appl. No.: 09/401,801

(22) Filed: Sep. 22, 1999

(30) Foreign Application Priority Data

Sep. 25, 1998 (JP) .......................................... 10-271732

(51) Int. Cl.[7] .............................................. A61B 5/00
(52) U.S. Cl. ...................................... 600/300; 128/904
(58) Field of Search ............................... 600/300–301, 600/481, 500, 509–515, 529, 532, 538, 544–545; 705/2–4; 128/900, 903–904, 920–925; 607/30–32, 29, 60

(56) References Cited

U.S. PATENT DOCUMENTS 5,255,187 A * 10/1993 Sorensen .................... 600/300
5,410,471 A * 4/1995 Alyfuku et al. ............. 600/300
5,544,649 A * 8/1996 David et al. ................ 600/301
5,711,297 A * 1/1998 Iliff ............................. 600/300
5,720,770 A * 2/1998 Nappholz et al. ........... 128/903
6,137,675 A * 10/2000 Perkins ........................ 128/876
6,206,829 B1 * 3/2001 Iliff ............................. 600/300
6,225,901 B1 * 5/2001 Kail, IV ..................... 128/904

* cited by examiner

*Primary Examiner*—Kevin Shaver
*Assistant Examiner*—Michael Astorino
(74) *Attorney, Agent, or Firm*—Arent Fox Kintner Plotkin & Kahn, PLLC

(57) ABSTRACT

A medical monitoring system has a first detecting device provided at a place where a subject exists, for detecting organic condition of the subject, a diagnosing device for diagnosing health condition of the subject based on the organic condition detected by the first detecting device and for producing organic data. A transmitting system is provided for transmitting the organic data to a service center, and a second diagnosing device is provided in the service center for diagnosing the health condition of the subject based on the organic data.

16 Claims, 2 Drawing Sheets

MEDICAL MONITORING SYSTEM

BACKGROUND OF THE INVENTION

The present invention relates to a medical monitoring system wherein a subject to be diagnosed is located outside medical facilities, the subject being, for example, a patient residing at home, or a driver or a operator on railway vehicles, vessel, or an aircraft, and the organic information of the subject is detected to watch over the health thereof.

There has recently been developed a medical monitoring system wherein organic information, for example an electrocardiogram, of a subject who is not at a medical facility is transmitted to a medical service center by way of such a transmission system as a telephone line. The health of the subject can be monitored using the transmitted organic information.

The medical monitoring system is used to continuously monitor the health of the aged living alone by employing the medical information such as the electrocardiogram or blood pressure. Any symptom which indicates a decline in health is reported to the medical facility, thereby enabling to send a doctor to the subject. In the case where organic information of a driver on duty on a public transportation system, for example a bus, is monitored, when a symptom indicating a deterioration of health is detected, measures are taken to relieve the driver of his duty.

Japanese Patent Application Laid Open 8-38435 discloses a conventional monitoring system for health care of a patient at home, and Japanese Patent Application Laid Open 6-22914 discloses a system for detecting organic information of an operator on railway vehicles.

The above described conventional monitoring systems each thus monitors the health at the service center dependent on electrocardiogram data and blood pressure data transmitted from electrocardiograph and sphygmomanometer provided at a home of a patient or at a seat of a driver of a motor vehicle.

However, it is difficult to diagnose one's health based only on measured data of the electrocardiogram and blood pressure in practice. More particularly, it is extremely difficult to diagnose arrhythmia of heart dependent only on the data of the electrocardiogram, and often results in erroneous diagnosis. In addition, due to the malfunctioning of the electrocardiograph and sphygmomanometer, there may occur a deficiency or error in the measured data obtained from the electrocardiograph and sphygmomanometer, which becomes a hindrance when attempting to accurately diagnose the health of the subject.

On the other hand, if the number of the measured data is increased to improve the accuracy of the diagnosis, there occur problems of rise in cost and increase in burden for data processing.

SUMMARY OF THE INVENTION

An object of the present invention is to provide a medical monitoring system wherein the above-described problems are resolved so that the health of the subject who is outside a medical facility can be accurately diagnosed, and the subject may receive an appropriate treatment.

According to the present invention, there is provided a medical monitoring system wherein health condition of a subject is monitored at a place away from where the subject exists, comprising, first detecting means provide data place where a subject exists, for detecting organic condition of the subject, first diagnosing means for diagnosing health condition of the subject based on the organic condition detected by the first detecting means and for producing first organic data, first transmitting means for transmitting the first organic data to.a service center, second detecting means for detecting visual condition of the subject or audio condition based on voice of the subject and for producing second organic data, and second transmitting means for transmitting the second organic data to the service center, second diagnosing means provided in the service center for diagnosing the health condition of the subject based on the first and second organic data.

The place where the subject exists is a residence of the subject.

The place where the subject exists is a seat of a driver of transportation means.

The transportation means is provided with a Global Positioning System.

The health condition is classified into a plurality of levels beforehand and set in the second diagnosing means.

The present invention further provides a medical monitoring system wherein health condition of a subject is monitored at a place away from where the subject exists, comprising, first detecting means provided at a place where a subject exists, for detecting organic condition of the subject and for producing first organic data, first transmitting means for transmitting the first organic data to a service center, second detecting means for detecting visual condition of the subject or audio condition based on voice of the subject and for producing second organic data, second transmitting means for transmitting the second organic data to the service center, and diagnosing means provided in the service center for diagnosing the health condition of the subject based on the first and second organic data.

These and other objects and features of the present invention will become more apparent from the following detailed description with reference to the accompanying drawings.

DETAILED DESCRIPTION OF THE PREFERRED EMBODIMENT

Figure 1:
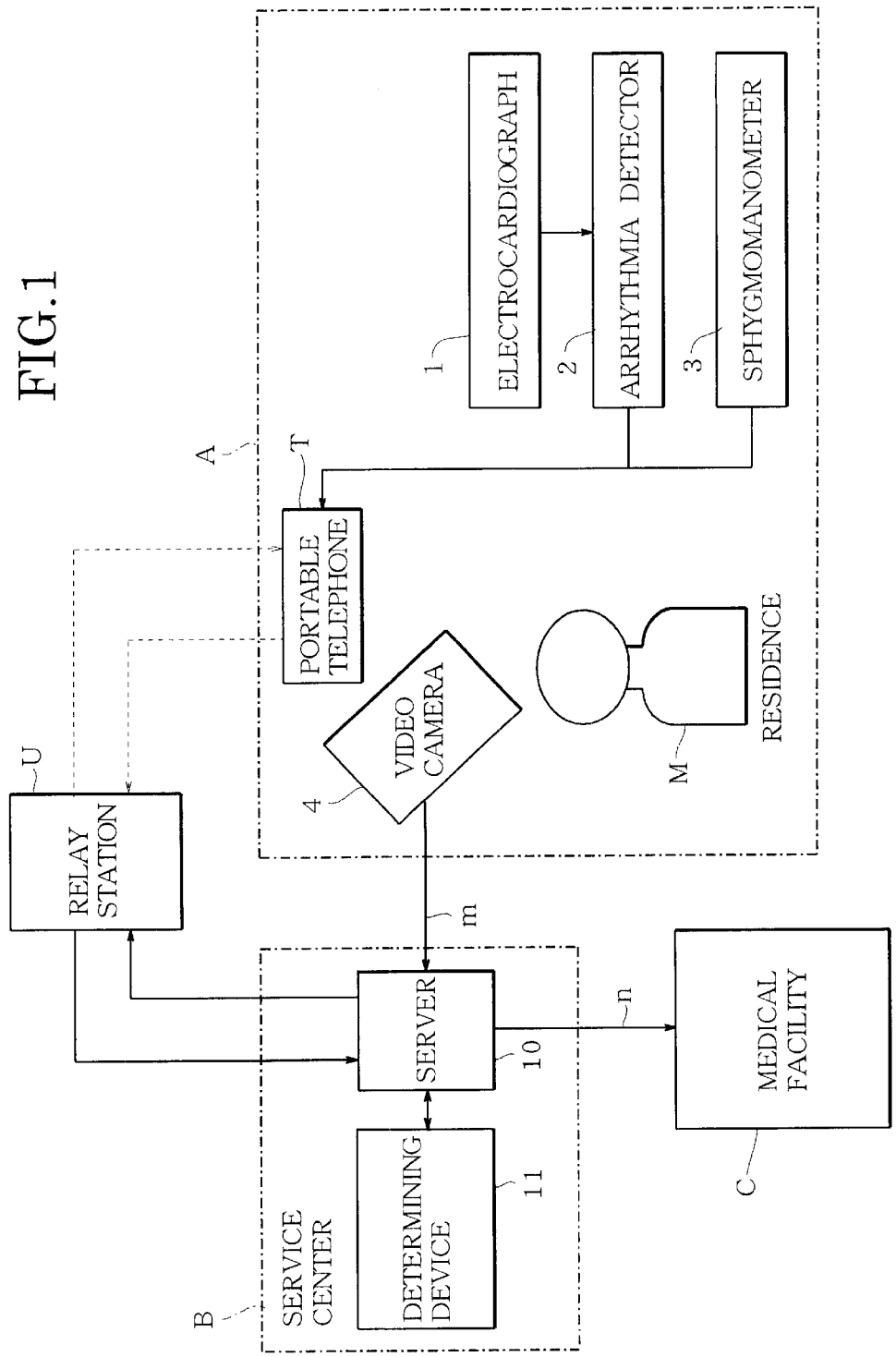
FIG. 1 is a block diagram showing an embodiment of a medical monitoring system of the present invention.

FIG. 1 shows an embodiment of the present invention which is applied to a medical monitoring system for a person residing at home.

Referring to FIG. 1, at a residence A of a subject M, there is provided an electrocardiograph 1, arrhythmia detector 2 connected to the electrocardiograph 1, sphygmomanometer 3, and a video camera 4. A portable telephone T capable of transmitting packet is also provided at the residence A.

At a service center B, there is provided a server 10 having organic data of the subject M, and a determining device 11 connected to the server 10 for diagnosing the health of the subject M based on the organic data applied from the server 10, the operation of which will be described later in detail. Organic data may be physiological information measured or detected which relates to the condition of a subject, such as an EKG measurement, a blood pressure measurement, audio or visual data. The server 10 is connected to a relay station U, which receives radio waves from the portable telephone T, and also to the video camera 4 at the residence A through a telephone line m. The server 10 is further connected to a medical facility C through a transmission line n.

In operation, the monitoring system examines the electrocardiogram of the subject M at the residence A using the electrocardiograph 1. The arrhythmia detector 2 determines whether the subject has an arrhythmia based on the detected electrocardiogram data. If the arrhythmia is detected, the electrocardiogram data is set in the packet of the portable telephone T together with an identification code of the phone.

When the portable telephone T is connected to the service center B, the electrocardiogram data and the identification code are transmitted to the server 10 through the relay station U. The transmitted electrocardiogram data and the name of the subject specified by the identification code are stored in the server 10 and further applied to the determining device 11. The determining device 11 accordingly conducts a diagnosis on the health of the subject M based on the electrocardiogram data.

When the determining device 11 determines that further examination is necessary, the server 10 is connected to the video camera 4 provided at the residence A of the subject M. Thus, visual information such as a picture of the face of the subject taken by the video camera 4 and audio information, namely the voice of the subject picked up by a microphone provided on the video camera 4, are applied to the server 10 through the telephone line m.

At the same time, the server 10 is connected to the portable telephone T in accordance with the decision of the determining device 11. Accordingly, the blood pressure data of the subject M detected by the sphygmomanometer 3 is fed to the server 10 through the portable telephone T and the relay station U.

At the service center B, the determining device 11 conducts a comprehensive diagnosis based on the electrocardiogram data, blood pressure data, visual information and audio information which are applied to the server 10, and classifies the health condition of the subject into three levels.

More particularly, there is provided a Level 1 where the health of the subject M is not a matter of particular concern, so that the determining device 11 sends a message for precaution, a Level 2 where since a treatment is necessary although not urgent, a message urging the subject to have his condition diagnosed and treated at the medical facility is sent, and a Level 3 where the condition of the subject is determined as a matter of emergency, thereby contacting the medical facility to send an ambulance to the residence A of the subject.

Therefore, when the determining device 11 determines the condition of the subject M as being at the Level 2, the server 10 sends the message as above to the portable telephone T of the subject. At the same time, each of the organic data is transmitted to the medical facility which is specified in the message sent to the subject M.

When the determining device 11 determines the condition of the subject M as being at the Level 3, the server 10 contacts the medical facility or the authorities to have the ambulance sent to the residence A of the subject M at once. At the same time, each of the organic data is transmitted to the medical facility which is specified when the ambulance is calling for.

Although the present embodiment is adapted to detect the arrhythmia of the subject M by the arrhythmia detector 2 provided at the residence A and to transmit the electrocardiogram data to the service center B when the arrhythmia is detected, the present invention may be modified to intermittently transmit the electrocardiogram data to the service center B and detect the arrhythmia at the determining device 11.

Figure 2:
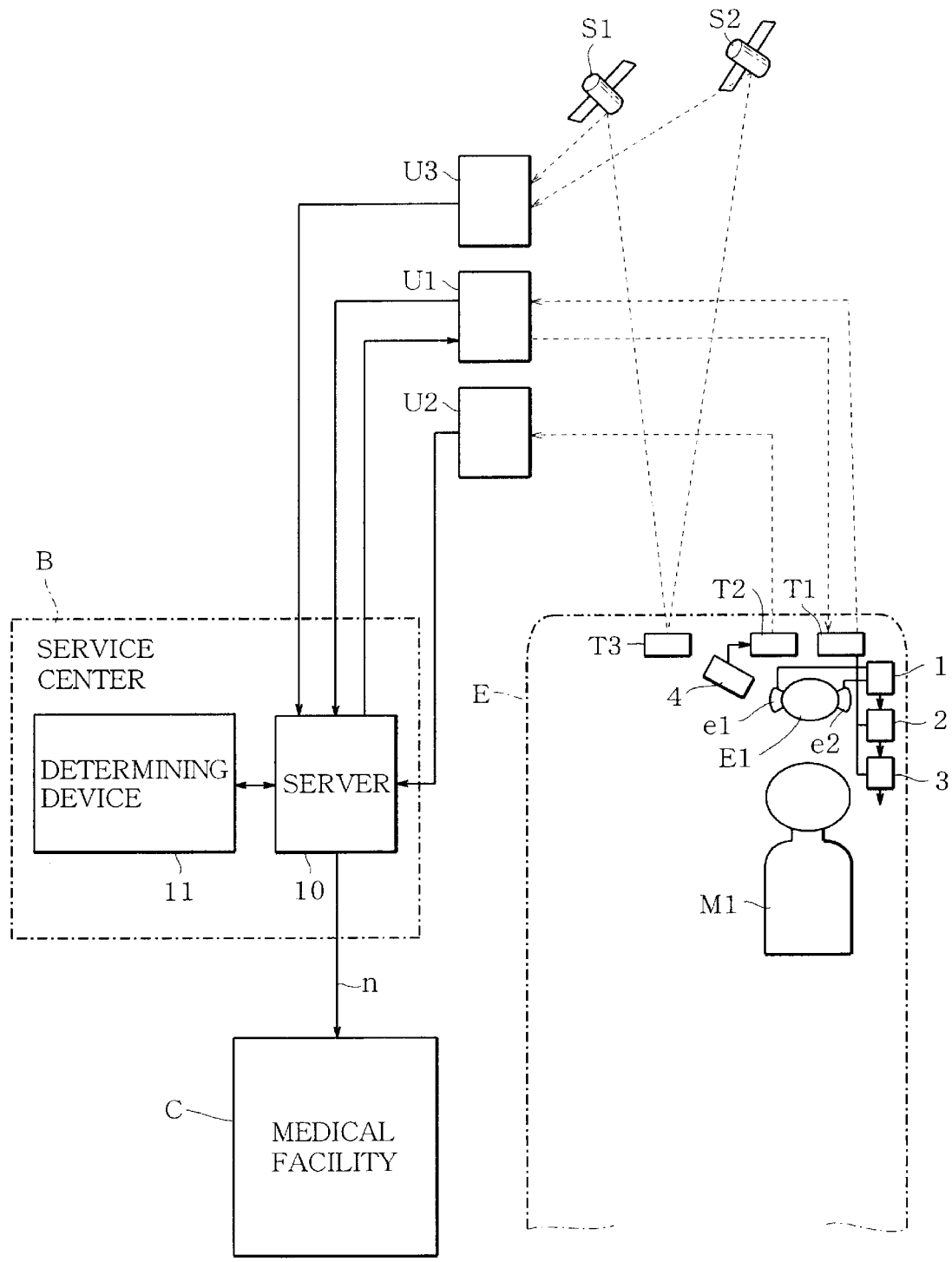
FIG. 2 is a block diagram showing a second embodiment of the present invention.

FIG. 2 shows the second embodiment of the present invention which is applied to a medical monitoring system mounted on a driver's seat of a bus for monitoring the health of a bus driver M1 on duty.

Referring to FIG. 2, similar to the first embodiment, the electrocardiograph 1, arrhythmia detector 2, sphygmomanometer 3, and the video camera 4 are mounted on a bus E at the driver's seat. A portable telephone T1 capable of transmitting packet, automotive radio transmitter T2 connected to the video camera, and a Global Positioning System (GPS) sensor T3 are further provided at the seat. The electrocardiograph 1 is connected to a potentiometric pulse sensor having a pair of electrodes e1 and e2 mounted on a steering wheel E1 of the bus E so as to measure the potential difference between both hands of the driver M1 holding the steering wheel E1.

The service center B has the same construction as the service center of FIG. 1, the sections thereof identified by the same references. Namely, the server 10 having organic data of the driver M1, and the determining device 11 connected to the server 10 are provided. The server 10 is connected to the medical facility C through the transmission line n.

In addition, the server is connected to a relay station U1 which receives radio waves from the portable telephone T1, and to a relay station U2 which is connected to the video camera 4 on the bus E through the automotive radio transmitter T2. The server 10 is further connected to a ground control station U3 which receives the radio waves applied from the GPS sensor T3 on the bus E through satellites S1 and S2 to detect the position of the bus E.

The monitoring system continuously detects the electrocardiogram of the driver M1 using the electrocardiograph 1. More particularly, the electrocardiograph 1 measures the potential difference between both hands of the driver with the pair of electrodes e1 and e2 thereof, which is mounted on the steering wheel E1 held by the driver. The arrhythmia detector 2 determines whether the driver M1 has an arrhythmia based on the detected electrocardiogram data. If the arrhythmia is detected, the electrocardiogram data is set in the data packet of the portable telephone T1 together with an identification code of the phone.

When the portable telephone T1 is connected to the service center B, the electrocardiogram data and the identification code is transmitted to the server 10 through the relay station U1. The transmitted electrocardiogram data and the name of the driver M1 specified by the identification code of the portable telephone are stored in the server 10 and further applied to the determining executes the device 11 as in the embodiment shown in FIG. 1. The determining device 11 accordingly conducts a diagnosis on the health of the driver M1 based on the electrocardiogram data.

When the determining device 11 determines that further examination is necessary, the server 10 is connected to the video camera 4 on the bus E through the relay station U2 and the automotive radio transmitter T2. Thus, visual information such as a picture of the face of the driver M1 taken by the video camera 4 and audio information, namely the voice of the driver picked up by a microphone provided on the video camera 4, are applied to the server 10.

At the same time, the server 10 is connected to the portable telephone T1 in accordance with the decision of the determining device 11. Accordingly, the bloodpressure data of the driver M1 detected by the sphygmomanometer 3 is fed to the server 10 through the portable telephone T1 and the relay station U1.

The determining device 11 at the service center B conducts a comprehensive diagnosis based on the electrocardiogram data, blood pressure data, visual information and audio information which are applied to the server 10, and classifies the health condition of the driver into three levels similarly to the first embodiment.

More particularly, at the Level 1, the health of the driver M1 is not a matter of particular concern so that a message for precaution is sent. At the Level 2, since a treatment is necessary although not urgent, a message urging the driver to have his condition diagnosed and treated at the medical facility is sent. At the Level 3, the condition of the driver is determined as a matter of emergency, so that a message is sent warning the driver to stop driving the bus E immediately, and the medical facility is contacted to send the ambulance.

Therefore, when the determining device 11 determines the condition of the subject M as being at the Level 2, the server 10 sends the message as above to the portable telephone T1 of the driver M1. At the same time, each of the organic data is transmitted to the medical facility which is specified in the message to the driver M1.

When the determining device 11 determines the condition of the driver M1 as being at the Level 3, the server 10 transmits the message through the portable phone T1 or the radio transmitter T2 to warn the driver to stop driving the bus E at once. In addition, the ambulance is sent to the bus E and each of the organic data is transmitted to the medical facility which is specified when calling for the ambulance.

The ground control station U3 receives radio waves from the GPS sensor T3 on the bus E through the satellites S1 and S2 and determines the position of the bus. When sending the ambulance to the bus E, the detected position data is transmitted to the server 10 at the service center B which further transmits the data to the ambulance, thereby enabling to hasten the time of arrival of the ambulance.

In the above described medical monitoring system mounted on a vehicle, a system of Advanced Safety Vehicle (ASV) may be incorporated, in which case a remote controlled control device is mounted on the bus E. Hence when the determining device 11 determines the condition of the driver M1 as being at Level 3, by a remote control from the service center B, the bus E may be compulsorily operated to decrease the speed or to stop.

Although the present embodiment is adapted to detect the arrhythmia of the driver M1 by the arrhythmia detector 2 provided on the bus E and to transmit the electrocardiogram data to the service center B when the arrhythmia is detected, the present invention may be modified to transmit the electrocardiogram data to the service center B at proper times by way of the portable telephone T1 and detect the arrhythmia at the determining device 11.

The potentiometric pulse sensor provided on the bus E for detecting the electrocardiogram of the driver M1 may be substituted by other devices such as an infrared pulse sensor.

The medical monitoring system of the second embodiment shown in FIG. 2 may be applied for monitoring an operator on a vessel and aircraft.

While the invention has been described in conjunction with preferred specific embodiment thereof, it will be understood that this description is intended to illustrate and not limit the scope of the invention, which is defined by the following claims.

What is claimed is:
1. A medical monitoring system for monitoring a health condition of a subject to be diagnosed at a place remote from where the subject is located, comprising:
   first detecting means, disposed at the place where the subject exists, for detecting first organic information of the subject;
   second detecting means, disposed at the place where the subject exists, for detecting second organic information of the subject:
   a service center, being remote from the place where the subject exists, for performing a predetermined diagnosis on the subject based on the first and second organic information; and
   communication means for connecting the first and second detecting means to the service center in a communicable manner,
   wherein the service center includes a server for receiving and storing the first and second organic information, diagnosing means for diagnosing the health condition of the subject based on the first and second organic information, classification means for classifying the health condition into one of predetermined levels based on a result of diagnosis made by the diagnosing means, and output means for performing a predetermined outputting process in one of a plurality of notification modes corresponding to the predetermined levels in accordance with a classified level,
   wherein the diagnosing means includes first diagnosing means for diagnosing the health condition and making a first diagnosis based on the first organic information, and second diagnosing means for further diagnosing the health condition and making a second diagnosis based on the second organic information,
   wherein the service center requests the second organic information to the second detecting means when the server determines that the second diagnosis is necessary based on the first diagnosis.
2. The medical monitoring system according to claim 1, wherein contents of the notification modes are changed in accordance with the plurality of levels.
3. The medical monitoring system according to claim 1, wherein said second organic information comprises visual information and/or audio information of the subject.
4. The medical monitoring system according to 2 or 3, wherein the subject is located in a vehicle.
5. The medical monitoring system according to claim 4, wherein the first and second detecting means and the communication means are located at a seat in a vehicle.
6. The medical monitoring system according to claim 1, wherein said output means notifies the subject of no health problem being present when diagnosis done by the second diagnosing means does not indicate a health problem, but transmits the first and second organic information and visual information and/or audio information of the subject to a medical attendance when diagnosis done by the second diagnosing means indicates a health problem exists.
7. The medical monitoring system according to claim 1, wherein the second diagnosing means diagnoses the health condition of the subject based on the first and second organic information.
8. The medical monitoring system according to any one of claims 1, 2 and 3, wherein the communication means has a global positioning system.
9. A medical monitoring method for monitoring a health condition of a subject to be diagnosed at a place remote from where the subject is located, comprising the steps of:

detecting first organic information of the subject;

communicating the detected first organic information with a service center which exists at the place remote from where the subject is located;

storing the communicated organic information of the subject into a server of the service center;

first diagnosing the subject based on the first organic information stored into the server in the service center;

classifying the health condition of the subject into one of predetermined levels based on a result of diagnosis made by the service center; and notifying one of a plurality of notification modes corresponding to the predetermined levels in accordance with a classification level, wherein the method further comprises the steps of:

requesting a second organic information of the subject from the service center when the service center determines that the second organic information is necessary in order to diagnose the subject;

detecting the second organic information of the subject;

communicating the detected second organic information with the service center;

storing the communicated second organic information of the subject into the server of the service center; and second diagnosing the health condition of the subject based on the second organic information.

10. The medical monitoring method according to claim 9, wherein contents of the notification modes are changed in accordance with the plurality of levels.

11. The medical monitoring method according to claim 9, wherein said second organic information comprises visual information and/or audio information of the subject.

12. The medical monitoring method according to claim 11, wherein the second diagnosing step diagnoses the health condition of the subject based on the first and second organic information.

13. The medical monitoring method according to claim 12, wherein the service center notifies the subject of no health problem being present when diagnosis done by the second diagnosing step does not indicate a health problem, but transmits the organic information and the visual information and/or information of the subject to a medical attendance when diagnosis done by the second diagnosing step indicates a health problem to be attended.

14. The medical monitoring system according to any one of claims 9, 10, 11, 12 and 13, wherein the subject is located in a vehicle.

15. The medical monitoring method according to claim 14, wherein detecting means for detecting the first and second organic information of the subject and the communication means for allowing the subject to communicate with the service center are located at a seat in the vehicle.

16. The medical monitoring method according to claim 15, wherein the communication means has a global positioning system.

* * * * *